| United States Patent [19] | [11] | 4,157,451 |
|---|---|---|
| Ohloff et al. | [45] | Jun. 5, 1979 |

[54] PROCESS FOR THE PREPARATION OF IPSDIENOL

[75] Inventors: Günther Ohloff; Wolfgang K. Giersch, both of Bernex/Geneva, Switzerland

[73] Assignee: Firmenich, S.A., Geneva, Switzerland

[21] Appl. No.: 849,269

[22] Filed: Nov. 7, 1977

[30] Foreign Application Priority Data

Nov. 12, 1976 [CH] Switzerland .................. 14263/76

[51] Int. Cl.² ............................................ C07C 33/02
[52] U.S. Cl. .................................................. 569/875
[58] Field of Search ........................................ 568/875

[56] References Cited

U.S. PATENT DOCUMENTS

| 2,972,632 | 2/1961 | Bain et al. ............................ 568/820 |
| 2,972,633 | 2/1961 | Klein .................................... 568/875 |
| 3,240,821 | 3/1966 | Ohloff et al. ......................... 568/875 |

FOREIGN PATENT DOCUMENTS 1019649  2/1966  United Kingdom .................... 568/875

*Primary Examiner*—Joseph E. Evans
*Attorney, Agent, or Firm*—Scully, Scott, Murphy & Presser

[57] ABSTRACT

Short synthesis for the preparation of 2-methyl-6-methylene-octa-2,7-dien-4-ol, better known under the name of ipsdienol, a bark beetle pheromone, starting from verbenone.

5 Claims, No Drawings

PROCESS FOR THE PREPARATION OF IPSDIENOL

SUMMARY OF THE INVENTION

The present invention provides processes for the preparation of optically active 2-methyl-6-methylene-octa-2,7-dien-4-ol, a bark beetle sex pheromone, which processes make use of optically active dextro- or levo-verbenone. By way of a three-step synthesis verbenone is converted into the desired epimer via the formation of iso-verbenone and subsequently iso-verbenol which compound is later pyrolyzed to yield the desired octadienol.

THE INVENTION

The present invention relates to a process for the preparation of 2-methyl-6-methylene-octa-2,7-dien-4-ol which process consists in the step of subjecting to pyrolysis isoverbenenol, a bicyclic carbinol of formula

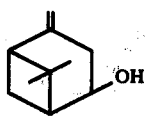
(I)

The present invention relates further to a process for the preparation of optically active S(+) and R(−) enantiomers of 2-methyl-6-methylene-octa-2,7-dien-4-ol of formula

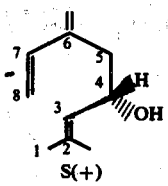
S(+)

and respectively of formula

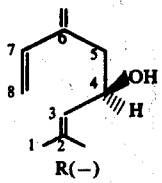
R(−)

which process comprises the step of subjecting levo- and respectively dextro-rotatory isoverbenol to pyrolysis. Another object of the present invention consists in a process for the preparation of the S(+) enantiomer of 2-methyl-6-methylene-octa-2,7-dien-4-ol which comprises the following subsequent reaction steps:

a. isomerizing the cyclic double bond of an unsaturated ketone of formula

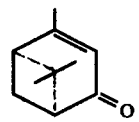
(IIa)

by means of a basic isomerizing agent to obtain the compound of formula

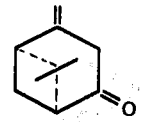
(IIIa)

b. reducing the thus obtained compound (IIIa) by means of an alkali metal borohydride or aluminohydride to give (−)-cis-isoverbenol of formula

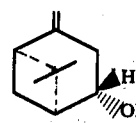
(IVa)

and c. heating (−)-cis-isoverbenol thus obtained at a temperature of from about 400° to 700° C. for a period of time sufficient to produce said S(+) enantiomer of 2-methyl6-methylene-octa-2,7-dien-4-ol, or alternatively a'. isomerizing the cyclic double bond of an unsaturated ketone of formula

(IIb)

by means of a basic isomerizing agent to obtain the compound of formula

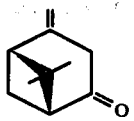
(IIIb)

b'. reducing the thus obtained compound (IIIb) by means a member selected from the group consisting of aluminium isopropoxide in isopropanol and an alkali metal in liquid ammonia to give (−)-trans-isoverbenol of formula

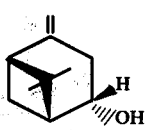
(IVb)

and c'. heating (−)-trans-isoverbenol thus obtained at a temperature of from about 400° to 700° C. for a period of time sufficient to produce said S(+) enantiomer of 2-methyl-6-methylene-octa-2,7-dien-4-ol.

Still another object of the present invention relates to a process for the preparation of the R(−) enantiomer of 2-methyl-6-methylene-octa-2,7-dien-4-ol which comprises the following subsequent steps:

w. isomerizing the cyclic double bond of an unsaturated ketone of formula

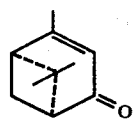 (IIa)

by means of a basic isomerizing agent to obtain the compound of formula

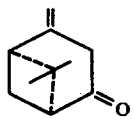 (IIIa)

y. reducing the thus obtained compound (IIIa) by means of a member selected from the group consisting of aluminium isopropoxide in isopropanol and an alkali metal in liquid ammonia to give (+)-trans-isoverbenol of formula

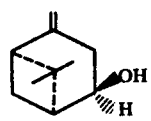 (IVc)

and z. heating (+)-trans-isoverbenol thus obtained at a temperature of from about 400° to 700° C. for a period of time sufficient to produce said R(−) enantiomer of 2-methyl-6-methylene-octa-2,7-dien-4-ol, or alternatively w'. isomerizing the cyclic double bond of an unsaturated ketone of formula

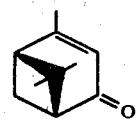 (IIb)

by means of a basic isomerizing agent to obtain the compound of formula

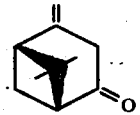 (IIIb)

y'. reducing the thus obtained compound (IIIb) by means of an alkali metal borohydride or aluminohydride to give (+)-cis-isoverbenol of formula

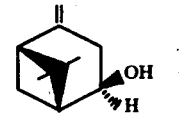 (IVd)

and z'. heating (+)-cis-isoverbenol thus obtained at a temperature of from about 400° to 700° C. for a period of time sufficient to produce said R(−) enantiomer of 2-methyl-6-methyleneocta-2,7-dien-4-ol.

PREFERRED EMBODIMENTS OF THE INVENTION

The above defined processes of the invention are better illustrated by the following reaction scheme.

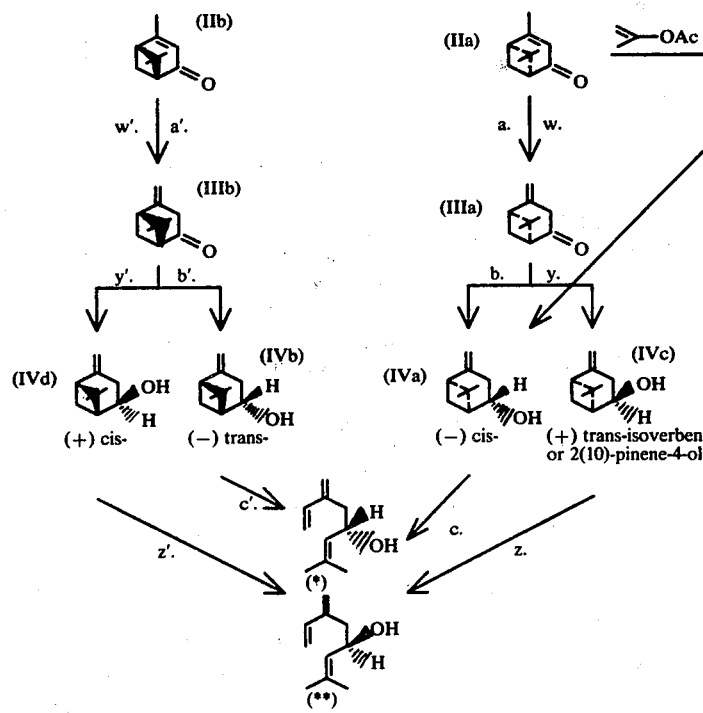

Reaction Scheme

Ac = acetyl
(*) S(+)-ipsdienol
(**) R(−)-ipsdienol

The first step of the above defined processes consists in isomerizing the endocyclic double bond of optically active levo- or dextro-verbenone, or (−)-2-pinene-4-one (IIa) and (+)-2-pinene-4-one (IIb), respectively, in order to convert these latter derivatives into the corresponding optically active isomers of 2(10)-pinene-4-one (IIIa) and (IIIb). According to the invention, said isomerization is effected by means of a basic agent, for instance by means of an alkali metal hydride or alkoxide. Suitable basic isomerization agents include sodium hydride, sodium methoxide or potassium terbutoxide in the presence of an inert organic solvent.

According to steps b and y or b' and y' of the process of the invention, (−)-2(10)-pinene-4-one (IIIa) and (+)-2(10)-pinene-4-one (IIIb) thus obtained are then subjected to the action of stereoselective reduction reagents in order to enable the formation of corresponding isoverbenols having the desired steric configuration. Thus, by reducing levo-2(10)-pinene-4-one (IIIa) by means of sodium or potassium borohydride or aluminohydride, the cis-(−)-enantiomer (IVa) or 2(10)-pinene-4-ol, also known as "isoverbenol", is isolated. In contradistinction therefrom, by carrying out the reduction of compound (IIIa) by means of aluminium isopropoxide in isopropanol there is obtained trans(+)-2(10)-pinene-4-ol(IVc) [see in this respect: Schimmel Berichte 1940, 42; idem 1942/43, 50].

In an analogous way, by reducing dextro-rotatory 2(10)-pinene-4-one (IIIb) by means of aluminium isopropoxide in isopropanol (step b') there is obtained the corresponding trans(−)-enantiomer (IVb) of 2(10)-pinene-4-ol, whereas when said compound (IIIb) is reduced by using an alkali metal borohydride or aluminohydride, the 2(10)-pinene-4-ol obtained possesses the cis-(+) configuration.

The last step of the processes of the invention consists in heating the obtained 2(10)-pinene-4-ol at a temperature of from about 400° to 700° C. for a period of time sufficient to produce the desired optically active enantiomer of 2-methyl-6-methylene-octa-2,7-dien-4-ol. This step is effected according to current techniques, namely according to the procedure described e.g. in U.S. Pat. No. 2,972,638 and in Helv. Chim. Acta 54, 1813 (1971).

According to a preferred embodiment of the process of the invention, the above said operation is carried-out by injecting a solution of 2(10)-pinene-4-ol, in a inert organic solvent, at one of the extremities of a column which had been preliminarly heated at the desired pre-selected temperature. Usually, the operation can be carried-out under reduced pressure and the vapours of the thus formed pyrolysate are collected at the other extremity of the column by condensing them at very low temperature, e.g. by using traps cooled with dry-ice/acetone freezing mixture or liquid nitrogen.

Typically, there is used a quartz column filled with beads of the same material. The temperature used may vary within wide limits, e.g. between about 400° and 700° C., preferably of from 500° and 600° C., more preferably at about 550° C. The said temperature is a function of the length of the column used and depends particularly on the value of the applied pressure. The examples which follow will describe some of the preferred chosen parameters, it will be however understood by those skilled in the art that values differing slightly from those indicated above may achieve analogous results. The time of pyrolysis is also a determining factor in obtaining good yields of end product. This can be varied by varying the length of the column and by varying the pressure.

Once collected, the condensed vapours of pyrolysate are purified according to the usual techniques, e.g. by extraction, fractional distillation or vapour phase chromatography. S(+)-2-methyl-6-methylene-octa-2,7-dien-4-ol is thus obtained by indifferently subjecting to pyrolysis cis- or trans(−)-2(10)-pinene-4-ol. On the contrary R(−)-2-methyl6-methylene-octa-2,7-dien-4-ol is obtained by pyrolyzing cis- or trans(+)-2(10)-pinene-4-ol.

Levo- and dextro-2-pinene-4-one, (IIa) and (IIb), the starting materials of the processes of the invention, are commercially available products (source:Glidden Co., Cleveland, Ohio, USA). Alternatively, the said compounds can be easily synthesized starting from levo- or dextro-$\alpha$-pinene, by oxidizing it in accordance with known methods. The invention is better illustrated by, but not limited to the following examples, wherein the temperatures are indicated in degrees centigrade and the abbreviations have the meaning common in the art.

General. Melting points are uncorrected. Preparative gaschromatography (GC) was performed on a Wilkens Aerograph, Model A 700 Autoprep, using glass columns of 3 m length ($\phi$ 4 mm, 10% Carbowax 20 M on Chromosorb W 95) at temperatures of 140°–210°. Specific rotations were measured on a Schmidt & Hansch, Polatronic 1 polarimeter 1 dm cell). IR. spectra were recorded by means of Perkin-Elmer A 21 and 720 spectrometers (films or CCl$_4$ solutions; bands are given in cm$^{-1}$). - NMR. spectra were measured on Varian A-60 and Bruker HFX-90 instruments. Normally, 3–4% solution in CCl$_4$ or CDCl$_3$ were used with Si(CH$_3$)$_4$ (=0 ppm) serving as the internal standard. Spectra are given in ppm ($\delta$), coupling constants are given in cycles per second and the multiplicities are abbreviated as follows: s=singlet, d=doublet, t=triplet, m=multiplet, br.=broad. Assignments are indicated in brackets. Mass spectra (MS) were determined on an Atlas CH4 instrument, electron energy: 70V).

Origin and chemical and optical purity of the substances used. - The (+)-$\alpha$-pinene used was obtained from Ega Chemie, Steinheim/Albuch (West-Germany) and had $\alpha_D^{20}$:+40.8° from which an $[\alpha]_D^{20}$:+46.6° at a density d$_4^{20}$ of 0.8569 ($[\alpha]_D^{25}$:+47.3°; $[\alpha]_D^{20}$:+55.2°, c=10/MeOH; $[\alpha]_D^{20}$:+56.3°, c=10/CHCl$_3$) was calculated. If the highest optical rotation of $[\alpha]_D^{25}$:+52.4° measured for $\alpha$-pinene is taken as 100%, the (+)-$\alpha$-pinene used by us had an optical purity of 91%. The (−)-$\alpha$-pinene used was obtained from Fluka AG, Buchs (Switzerland) and had $[\alpha]_D^{20}$:−41.9° ($[\alpha]_D^{20}$:−42.4°, c=10/MeOH; $[\alpha]_D^{20}$:−48°, c=10/CHCl$_3$) and an optical purity of 80%. The enantiomeric verbenones were prepared from the corresponding (+)-$\alpha$- and (−)-$\alpha$-pinenes, respectively, by Criegee oxidation [Angew. Chem. 70, 173 (1958) and J. Chem. Soc. 1961, 2232], subsequent saponification, isolation of the diastereoisomeric verbenols and oxidation with MnO$_2$ [J. Chem. Soc. 1960, 2864]. The optical rotation in methanol (c=10) of the products purified by GC. were as follows:

|  | $[\alpha]^{20}_D$: |
|---|---|
| (−)-cis-verbenol | −10.5° |
| (+)-trans-verbenol | +153° |
| (+)-verbenone | +248° |
| (+)-cis-verbenol | +8.7° |
| (−)-trans-verbenol | −121.3° |
| (−)-verbenone | −219°[1] |

[1] In CHCl₃ (c = 10) a value of $[\alpha]^{20}_D$: −217°, and in the absence of a solvent a value of $[\alpha]^{20}_D$: −218° were measured
verbenone = 2-pinene-4-one verbenol = 2-pinene-4-ol

EXAMPLE a'./w'. 100 g of (+)-verbenone were added dropwise under argon, with vigorous stirring, to a suspension of 60 g of NaH in 1000 ml of THF. After stirring for 55 h, the reaction mixture was poured into an ice-cold solution of 360 g of boric acid in 6 l of water and extracted with ether. The combined ethereal extracts were washed basefree with brine, the solvent was evaporated on a Büchi rotary evaporator, and the residue was subjected to vacuum distillation; b.p. 52°/0.01 mm; yield 88 g (88%); $[\alpha]_D^{20}$:+67.4° (c=10/MeOH). As shown by gas-chromatographic analysis the product obtained, (+)-2(10)-pinene-4-one, was free from impurities.

IR (film): 3080, 1723, 1650, 1461, 1388, 1298, 1270, 1242, 1198, 1098, 1028, 918, 880, 753.
NMR (CCl₄): 0.768 (s, 3H), 1.37 (s, 3H), 1.74 (m, 1H), 2.5 to 3.3 (m, 5H), 4.82 (m, 2H).
MS: M+150 (11), m/e 135 (4), 122 (5), 107 (16), 91 (12), 83 (100), 82 (23), 79 (20), 67 (12), 55 (34), 41 (13), 39 (16), 27 (13).

a./w. 25 g of (−)-verbenone were treated with 15 g of NaH in 250 ml of THF and the product then quenched in the manner described in the above section. (−)-2(10)-pinene-4-one was obtained in a yield of 21 g (84%); $[\alpha]_D^{20}$:−56°, c=10/MeOH. The spectra of this product were identical with those indicated for the (+)-enantiomer.

y'. 60 g of (+)-2(10)-pinene-4-one were added dropwise under argon to a stirred solution of 4.2 g of LiAlH₄ in 600 ml of ether. After refluxing for 1 h the mixture was cooled and poured into ice-cold dilute hydrochloric acid. The mixture was washed neutral with brine, the solvent was evaporated on a Buchi rotary evaporator, and the residue was distilled in vacuo; b.p. 110° (bath temperature)/0.01 mm; to yield 43 g (71%) of cis(+)-2(10)-pinene-4-ol; m.p. 62°-62.5°/petroleum ether; $[\alpha]_D^{20}$:+1.9° (c=10/MeOH).

IR (film): 3380, 3080, 1645, 1475, 1300, 1245, 1057, 1015, 937, 870, 850.
NMR (CCl₄): 0.97 (s, 3H), 1.28 (s, 3H), 2.0 to 3.3 (m, 6H), 2.0 (OH), 4.30 (m, 1H), 4.67 (m, 2H).
MS: M+152 (4); m/e 137 (6), 134 (14), 119 (18), 109 (22), 91 (27), 85 (100), 81 (25), 79 (25), 69 (19), 67 (23), 55 (19), 41 (43), 29 (15), 27 (15).

b. 20 g of (−)-2(10)-pinene-4-one were treated with 1.4 g of LiAlH₄ in 200 ml of ether in the manner described in section y'. above to give cis-(−)-2(10)-pinene-4-ol (bath temperature)/0.01 mm; yield: 19 g (94%); m.p. 62°-62.5°/petroleum ether; $[\alpha]_D^{20}$:−1.8 (c=10/MeOH). The spectra of the obtained product were identical with those of the compound obtained according to section y'. above.

y. To a solution of 3 g of (−)-2(10)-pinene-4-one in 100 ml of liquid ammonia (distilled from sodium), 20 ml of abs. THF, and 20 ml of ter-butyl alcohol, 2 g of lithium were added in small portions with vigorous stirring at −60°. The NH₃ was allowed to evaporate overnight, the residue was extracted with ether, and the extract was treated in the usual manner. B.p. 150° (bath temperature)/0.1 mm; trans (+)-2(10)-pinene-4-ol was obtained in an amount of 2.3 g in combination with the cis(−)-enantiomer and (−)-verbenone. Pure trans(+)-2(10)-pinene-4-ol had the following constants and spectra: $[\alpha]_D^{20}$:+10.8° (c=10/MeOH).

IR (CCl₄): 3360, 3080, 1650, 1045, 890.
NMR (CCl₄): 0.70 (s, 3H), 1.28 (s, 3H), 1.5 to 3.0 (m, 7H), 4.12 (t, J=7.6, 1H), 4.6 (br. s, 2H).
MS: M+152 (1.5), m/e 137 (1.5), 134 (2), 119 (5), 109 (11), 91 (10), 85 (100), 67 (13), 57 (7), 55 (7), 41 (28).

Alternatively, trans(+)-2(10)-pinene-4-ol is obtained as follows: 9 g of (−)-2(10)-pinene-4-one and 25 g of aluminium isopropoxide were refluxed for 3 h with mechanical stirring in 300 ml of isopropanol. The solvent was then slowly distilled off on a Vigreux, the residue poured into ice-water, the mixture was extracted with ether, and the ethereal extract treated in the usual manner; b.p. 150° (bath temperature)/0.1 mm. The desired trans(+)-2(10)-pinene-4-ol was obtained in a 14% yield. The pure product could be separated from the other components of the obtained mixture by preparative GC from simultaneously formed cis-(−)-isomer, cis(+)-verbenol and trans(−)-verbenol. The spectra of the sample so obtained were identical with those of the sample of the product obtained according to the above section.

b'. By treating 9 g of (+)-2(10)-pinene-4-one in the manner described above, 8 g of a mixture of alcohols corresponding to that obtained from (−)-2(10)-pinene-4-one but having the opposite sign of optical rotation from which trans(−)-2(10)-pinene-4-one could be isolated in pure form. $[\alpha]_D^{20}$:−11.4° (c=10/MeOH).

z. A solution of 300 mg of trans-(+)-2(10)-pinene-4-ol in 1.8 ml of pyridine was introduced into the pyrolysis oven described above [see also Chem. Ber. 93, 2673 (1960)]. The quartz tube of the oven was 25 cm long and partially filled with sintered quartz rings. The quartz tube was heated to 550° and its interior pressure reduced to 0.01 mm. The pyrolysate was collected in a trap cooled to −80°. After removal of the pyridine by distillation in a high vacuum at 20° the residue was chromatographed on silica gel, using hexane/ether 95:5 as the eluant, and then subjected to a further purification by preparative GC. (3 M Carbowax 15%/140°). In this way 120 mg (40%) of R-(−)-2-methyl-6-methylene-octa-2,7-dien-4-ol were obtained which showed the following physical and spectra constants: $[\alpha]_D^{20}$:−9° (c=9.8/MeOH).

IR (film): 3350, 3100, 1685, 1600, 1455, 1385, 1030, 1000, 920.
NMR (CCl₄): 1.63 (d, J=1, 3H), 1.7 (d, J=1, 3H), 2.0 (OH), 2.32 (d, J=6, 2H), 4.37 (d, t, J=6, J₂=8, 1H), 4.9 to 5.4 (m, 5H), 6.35 (d, d, J₁=11, J₂=17, 1H).
MS: M+152 (1), m/e 134 (2), 119 (4), 85 (100), 67 (13), 55 (8), 41 (32).

z'. The pyrolysis of 10 g of cis-(+)-2(10)-pinene-4-ol in the same manner yielded 4.8 g (48%) of R(−)-2-methyl6-methylene-octa-2,7-dien-4-ol with $[\alpha]_D^{20}$:−12° (c=10/MeOH).

c. 10 g of cis(−)-2(10)-pinene-4-ol were pyrolyzed as described in section z. above. Pure S(+)-2-methyl-6-methylene-octa-2,7-dien-4-ol was obtained in 42% yield; $[\alpha]_D^{20}$:+11.8 (c=10/MeOH). The spectra were identical with those of the R(—)-isomer as described in section z.

c'. By carrying-out the pyrolysis on trans-(—)-2(10)-pinene-4-ol in accordance with the above described procedure there was obtained the desired S(+)-2-methyl-6-methyleneocta-2,7-dien-4-ol in much the same yields.

A variant of one of the processes of the invention consists in preparing cis(—)-2(10)-pinene-4-ol (IVa) starting from (+)-2(10)-3-pinadien-4-yl acetate, a compound of formula

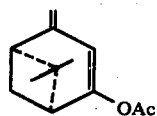

Ac = COCH₃ by reducing it by means of lithium aluminium hydride. The method followed is described hereinbelow:

i. 2 g of (—)-2-pinene-4-one were heated with 150 ml of isopropenyl acetate and a few crystals of p-toluenesulfonic acid and the acetone formed was removed by distillation through a Vigreux column. After distillation for 60 h the residue was taken up in ether, the ethereal extract was washed neutral and purified by distillation in vacuo; b.p. 150° (bath temperature)/0.1 mm; yield: 2.4 g (93%) of the desired acetate; $[\alpha]_D^{20}: +32.3°$ (c=9.5/MeOH).

IR (CCl₄): 1720, 1695, 1230, 885.

NMR (CCl₄): 0.935 (s, 3H), 1.4 (s, 3H), 2.1 (s, 3H), 4.68 (br. s, 2H), 5.7 (s, 1H).

MS: M+192 (1), m/e 150 (90), 135 (100), 108 (90), 107 (74), 91 (20), 79 (15), 55 (21), 43 (63).

ii. 3.3 g of the obtained acetate, 0.5 g of LiAlH₄ and 50 ml of ether were refluxed for 1 h under argon. The reaction mixture was then poured into ice-cold dilute hydrochloric acid. The mixture was washed neutral with brine and then treated in the usual manner; b.p. 100° (bath temperature)/0.1 mm; yield: 2.2 g (86%). As shown by GC the product consisted of the pure cis-(—)-2(10)-pinene-4-ol the spectral data of which were identical with those of the sample obtained in section b. above.

What we claim is:

1. Process for the preparation of enantiomers of 2-methyl-6-methylene-octa-2,7-dien-4-ol which comprises the following steps:

(a) isomerizing the cyclic double bond of an unsaturated ketone of formulae

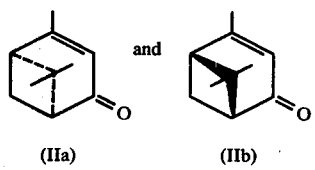

(IIa)     (IIb)

by means of a basic isomerizing agent to obtain a compound of formulae

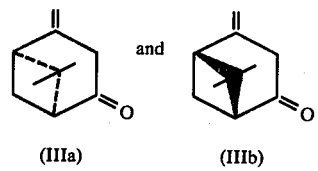

(IIIa)     (IIIb)

respectively;

(b) reducing the thus obtained compound to obtain (+) or (—)-cis-isoverbenol or (+) or (—)-trans-isoverbenol respectively; and (c) heating the thus obtained (—)-cis-and(—)-trans- or (+)-cis-and (+)-trans-isoverbenol products at a temperature of from about 400° to 700° C. for a period of time sufficient to produce respectively the S(+) or R(—) enantiomers of 2-methyl-6-methylene octa-2,7-dien-4-ol; said reduction of the formulae IIIa and IIIb compound being by means of an alkali metal borohydride or aluminohydride to obtain the (+)- and (—)-cis-isoverbenol and said reduction of the formulae IIIa and IIIb compound being by means of aluminum isopropoxide in isopropanol or an alkali metal in liquid ammonia to obtain the (—)- and (+)-trans-isoverbenol respectively.

2. Process for the preparation of the S(+) enantiomer of 2-methyl-6-methylene-octa-2,7-dien-4-ol which comprises the following subsequent reaction steps:

(a) isomerizing the cyclic double bond of an unsaturated ketone of formula

(IIb)

by means of a basic isomerizing agent to obtain the compound of formula

(IIIb)

(b) reducing the thus obtained compound (IIIb) by means of a member selected from the group consisting of aluminum isopropoxide in isopropanol and an alkali metal in liquid ammonia to give (—)-trans-isoverbenol of formula

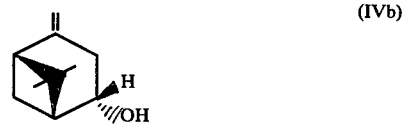

(IVb)

and (c) heating (—)-trans-isoverbenol thus obtained at a temperature of from about 400° to 700° C. for a period of time sufficient to produce said S(+) enantiomer of 2-methyl-6-methylene-octa-2,7-dien-4-ol.

3. Process for the preparation of the R(—) enantiomer of 2-methyl-6-methylene-octa-2,7-dien-4-ol which comprises the following subsequent steps:

(a) isomerizing the cyclic double bond of an unsaturated ketone of formula

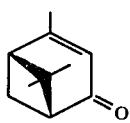

(IIb)

by means of a basic isomerizing agent to obtain the compound of formula

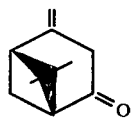

(IIIb)

(b) reducing the thus obtained compound (IIIb) by means of an alkali metal borohydride or aluminohydride to give (+)-cisisoverbenol of formula

(IVd)

and (c) heating (+)-cis-isoverbenol thus obtained at a temperature of from about 400° to 700° C. for a period of time sufficient to produce said R(−) enantiomer of 2-methyl-6-methylene-octa-2,7-dien-4-ol.

4. The process for the preparation of the S(+) enantiomer of 2-methyl-6-methylene-octa-2,7-dien-4-ol which comprises the following subsequent reaction steps:

(a) isomerizing the cyclic double bond of an unsaturated ketone of formula

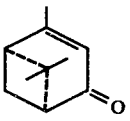

(IIa)

by means of a basic isomerizing agent to obtain the compound of formula

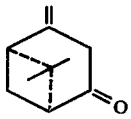

(IIIa)

(b) reducing the thus obtained compound (IIIa) by means of an alkali metal borohydride or aluminohydride to give (−)-cisisoverbenol of formula

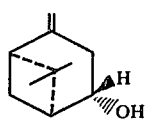

(IVa)

and (c) heating (−)-cis-isoverbenol thus obtained at a temperature of from about 400° to 700° C. for a period of time sufficient to produce said S(+) enantiomer of 2-methyl-6-methylene-octa-2,7-dien-4-ol.

5. Process for the preparation of the R(−) enantiomer of 2-methyl-6-methylene-octa-2,7-dien-4-ol which comprises the following subsequent steps:

(a) isomerizing the cyclic double bond of an unsaturated ketone of formula

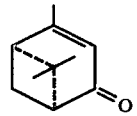

(IIa)

by means of a basic isomerizing agent to obtain the compound of formula

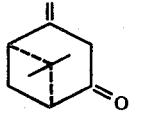

(IIIa)

(b) reducing the thus obtained compound (IIIa) by means of a member selected from the group consisting of aluminum isopropoxide in isopropanol and an alkali metal in liquid ammonia to give (+)-trans-isoverbenol of formula

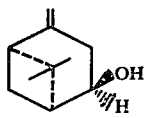

(IVc)

and (c) heating (+)-trans-isoverbenol thus obtained at a temperature of from about 400° to 700° C. for a period of time sufficient to produce said R(−) enantiomer of 2-methyl-6-methylene-octa-2,7-dien-4-ol.

* * * * *